United States Patent
Yamada (10) Patent No.: US 8,372,100 B2
(45) Date of Patent: Feb. 12, 2013

(54) ULTRASOUND SURGICAL APPARATUS AND CALIBRATION METHOD THEREFOR

(75) Inventor: Masashi Yamada, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 908 days.

(21) Appl. No.: 12/488,010

(22) Filed: Jun. 19, 2009

(65) Prior Publication Data

US 2010/0324580 A1 Dec. 23, 2010

(51) Int. Cl.
*A61B 18/18* (2006.01)
(52) U.S. Cl. .......................... 606/169; 606/34
(58) Field of Classification Search ............. 606/169, 606/27, 34
See application file for complete search history.

(56) References Cited

U.S. PATENT DOCUMENTS

| | | | |
|---|---|---|---|
| 5,406,503 A * | 4/1995 | Williams et al. | 702/106 |
| 5,808,396 A | 9/1998 | Boukhny | |
| 5,959,390 A | 9/1999 | Boukhny | |
| 2001/0029315 A1* | 10/2001 | Sakurai et al. | 600/101 |
| 2002/0165680 A1 | 11/2002 | Wiener et al. | |
| 2002/0193787 A1* | 12/2002 | Qin et al. | 606/34 |
| 2008/0194999 A1 | 8/2008 | Yamaha et al. | |
| 2010/0292573 A1* | 11/2010 | Tanaka | 600/439 |
| 2010/0312107 A1* | 12/2010 | Tanaka et al. | 600/439 |
| 2010/0312111 A1* | 12/2010 | Tanaka et al. | 600/443 |
| 2012/0136279 A1* | 5/2012 | Tanaka et al. | 601/2 |

FOREIGN PATENT DOCUMENTS

| | | |
|---|---|---|
| EP | 1 199 044 A1 | 4/2002 |
| JP | 2001-087278 | 4/2001 |
| JP | 2001-506527 * | 5/2001 |
| JP | 2002-177292 A | 6/2002 |
| JP | 2008-188160 | 8/2008 |
| JP | 2008-194457 | 8/2008 |
| WO | WO 98/26739 | 6/1998 |
| WO | WO 2005/094701 A1 | 10/2005 |

* cited by examiner

*Primary Examiner* — Linda Dvorak
*Assistant Examiner* — Jocelyn D Ram
(74) *Attorney, Agent, or Firm* — Scully, Scott, Murphy & Presser, P.C.

(57) ABSTRACT

An ultrasound surgical apparatus includes a handpiece which includes a probe provided with a proximal end portion mechanically coupled to an ultrasound transducer and a distal end portion used for treatment of a living tissue; a drive portion which outputs a drive signal; a detection portion which detects, in the drive signal, a cavitation level signal corresponding to a state of cavitation generated in a calibration solution, based on the drive signal of calibration signal strength corresponding to class information about the handpiece; a condition storage portion which stores calibration information; an output setting portion which sets the vibration strength; and a control portion which controls the drive portion so as to output the drive signal of drive signal strength corresponding to the vibration strength set by the output setting portion, based on the calibration information and the class information.

14 Claims, 7 Drawing Sheets

ULTRASOUND SURGICAL APPARATUS AND CALIBRATION METHOD THEREFOR

BACKGROUND OF THE INVENTION

1. Field of the Invention

The present invention relates to an ultrasound surgical apparatus used for treatment of living tissues by means of ultrasound vibrations and to a calibration method for the ultrasound surgical apparatus.

2. Description of the Related Art

Examples of ultrasound surgical apparatuses used for treatment of living tissues by means of ultrasound vibrations include an ultrasound-activated scalpel, ultrasound aspirator, ultrasound lithotriptor, and ultrasound trocar.

The ultrasound-activated scalpel is used to perform a coagulation process or dissection process by means of frictional heat generated when a tissue is grasped with a probe which performs ultrasound vibrations. The ultrasound-activated scalpel can operate at lower temperatures than an electrical surgical apparatus and thus causes less damage to tissues. A probe capable of high-frequency current conduction makes it easy to administer hemostatic treatment.

The ultrasound aspirator, which utilizes tissue selectivity of ultrasound, heats only fragile tissues with ultrasound vibrations and thereby emulsifies and aspirates the fragile tissues. This makes it possible to expose flexible tissues such as blood vessels without crushing.

The ultrasound lithotriptor breaks a stone or the like using an impact of ultrasound vibrations, with a probe vibrated by ultrasound being placed in direct contact with the stone or the like.

The ultrasound trocar reduces a contact overload on a living tissue using ultrasound vibrations and thereby enables puncture using a small amount of force. The ultrasound trocar, which can reduce bleeding by the coagulating effect of ultrasound vibrations, can make the field of view of an endoscope less liable to being blocked by bleeding from the abdominal wall.

Thus, ultrasound surgical apparatuses treat living tissues using ultrasound vibrations of a distal end portion of a probe joined to, i.e., mechanically coupled to, an ultrasound transducer.

With ultrasound surgical apparatuses, even if the ultrasound transducer is driven at a predetermined driving current, it was sometimes difficult to vibrate the distal end portion of the probe at a predetermined vibration strength depending on factors such as manufacturing variations, operating temperature, state of junction between the ultrasound transducer and probe, or aging of the system. Incidentally, to measure the vibration strength of ultrasound vibrations directly as amplitude, an expensive, special apparatus which uses laser Doppler effect was required, and thus it was difficult to check vibration strength at a treatment location before treatment.

International Publication No. WO 2005/094701 discloses an ultrasound irradiation method which detects state of cavitation based on a sound pressure signal to maintain a predetermined state of cavitation.

Also, Japanese Patent Application Laid-Open Publication No. 2001-87278 discloses an ultrasound aspirator which detects an actual output value (amount of amplitude) in a distal end portion of a probe based on load information about an ultrasound transducer and feeds the output value back to a controller.

BRIEF SUMMARY OF THE INVENTION

An ultrasound surgical apparatus according to an embodiment of the present invention includes: a handpiece equipped with an ultrasound transducer which generates ultrasound vibrations, and a probe which, being provided with a proximal end portion mechanically coupled to the ultrasound transducer and a distal end portion used for treatment of a living tissue, transmits the ultrasound vibrations generated by the ultrasound transducer from the proximal end portion to the distal end portion; a drive portion which outputs a drive signal to drive the ultrasound transducer; a detection portion which detects, in the drive signal, a cavitation level signal corresponding to a state of cavitation generated in a calibration solution by ultrasound emitted from the distal end portion, based on the drive signal of calibration signal strength corresponding to class information about the handpiece; a condition storage portion which stores calibration information which represents a relationship between drive signal strength and vibration strength of the distal end portion based on the calibration signal strength and the cavitation level signal; an output setting portion which sets the vibration strength of the distal end portion; and a control portion which controls the drive portion so as to output the drive signal of the drive signal strength corresponding to the vibration strength set by the output setting portion, based on the calibration information and the class information.

A calibration method for an ultrasound surgical apparatus according to another embodiment of the present invention includes: a preparation step of preparing a handpiece equipped with an ultrasound transducer which generates ultrasound vibrations, and a probe which, being provided with a proximal end portion mechanically coupled to the ultrasound transducer and a distal end portion used for treatment of a living tissue, transmits the ultrasound vibrations generated by the ultrasound transducer from the proximal end portion to the distal end portion, and connecting the ultrasound transducer with a drive portion which outputs a drive signal to the ultrasound transducer; a class information acquisition step of acquiring class information about the handpiece; a distal end portion immersion step of immersing the distal end portion in a calibration solution; a calibration drive signal supply step of supplying the ultrasound transducer with the drive signal of calibration signal strength corresponding to the class information; a cavitation level signal detection step of detecting, in the drive signal, a cavitation level signal corresponding to a state of cavitation generated in the calibration solution by ultrasound emitted from the distal end portion; a condition storage step of storing calibration information which represents a relationship between drive signal strength and vibration strength of the distal end portion based on the calibration signal strength and the cavitation level signal; an output setting step of setting the vibration strength of the distal end portion; and a treatment step of controlling the drive portion so as to output the drive signal of the drive signal strength corresponding to the vibration strength set by the output setting portion, based on the class information and the calibration information.

DETAILED DESCRIPTION OF THE PREFERRED EMBODIMENTS

First Embodiment

An ultrasound surgical apparatus 1 according to a first embodiment of the present invention will be described with reference to the drawings.

Figure 1:
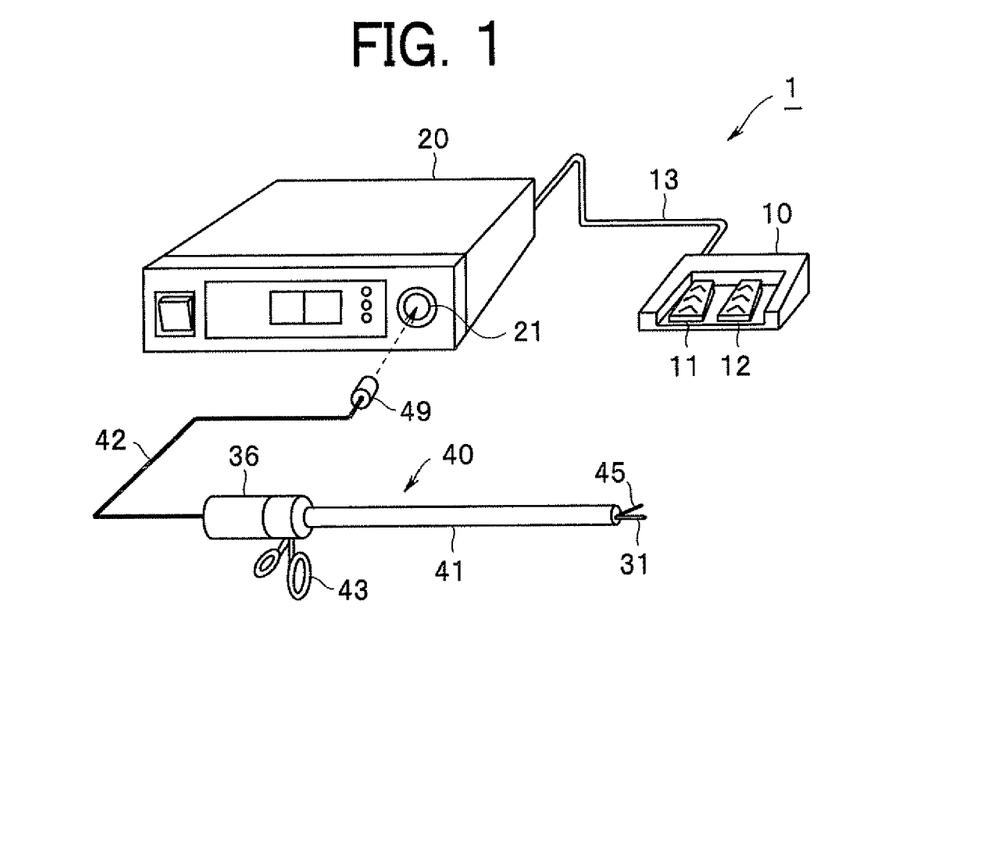
FIG. 1 is a perspective view showing an external configuration of an ultrasound surgical apparatus according to a first embodiment.
Figure 2:
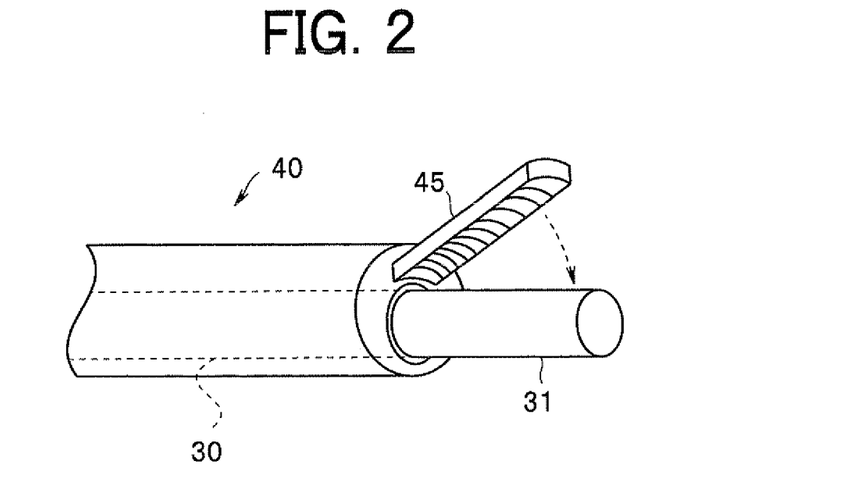
FIG. 2 is a perspective view illustrating a structure of a distal end portion of a probe of the ultrasound surgical apparatus according to the first embodiment.

As shown in FIGS. 1 and 2, the ultrasound surgical apparatus 1 according to the present embodiment is an ultrasound-activated scissors which include an apparatus body portion 20, a handpiece 40 connected to the apparatus body portion 20 via a cable 42, and a foot switch 10 connected to the apparatus body portion 20 via a cable 13. A connector 49 of the cable 42 is detachably connected to a socket 21 in the apparatus body portion 20. That is, the handpiece 40 to be used for a treatment is selected from among multiple handpieces and connected to the apparatus body portion 20. The foot switch 10 includes a switch 11 for coagulation procedures and a switch 12 for dissection procedures.

The handpiece 40 includes an ultrasound unit 36 which contains an ultrasound transducer (hereinafter also referred to as a "transducer;" see FIG. 3) 35, and a probe unit 41 whose distal end portion 31 is used for treatment of living tissues. A cylindrical, rod-shaped probe 30 is disposed in the probe unit 41. An operation handle 43 for use to operate a grasping portion 45 on a distal side is disposed on a proximal side of the probe unit 41.

As shown in FIG. 2, when a surgeon performs the operation of gripping the operation handle 43 (closing operation), the grasping portion 45 deforms in such a direction as to be pressed against the distal end portion 31. Using frictional heat generated by ultrasound vibrations, the surgeon performs a coagulation procedure or dissection procedure on a living tissue grasped between the grasping portion 45 and distal end portion 31.

Figure 3:
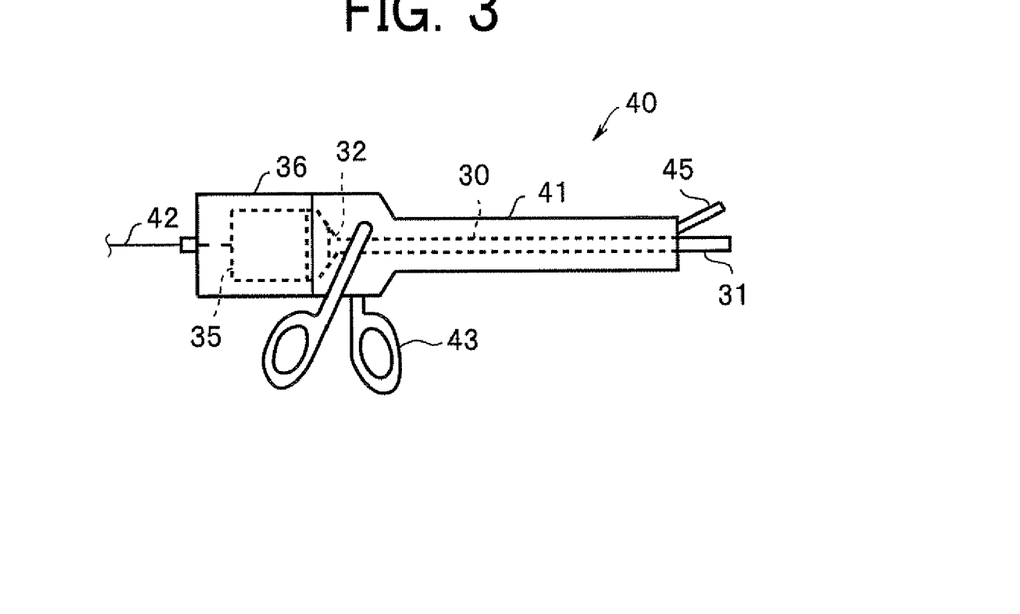
FIG. 3 is a schematic diagram illustrating a configuration of the probe of the ultrasound surgical apparatus according to the first embodiment.
Figure 4:
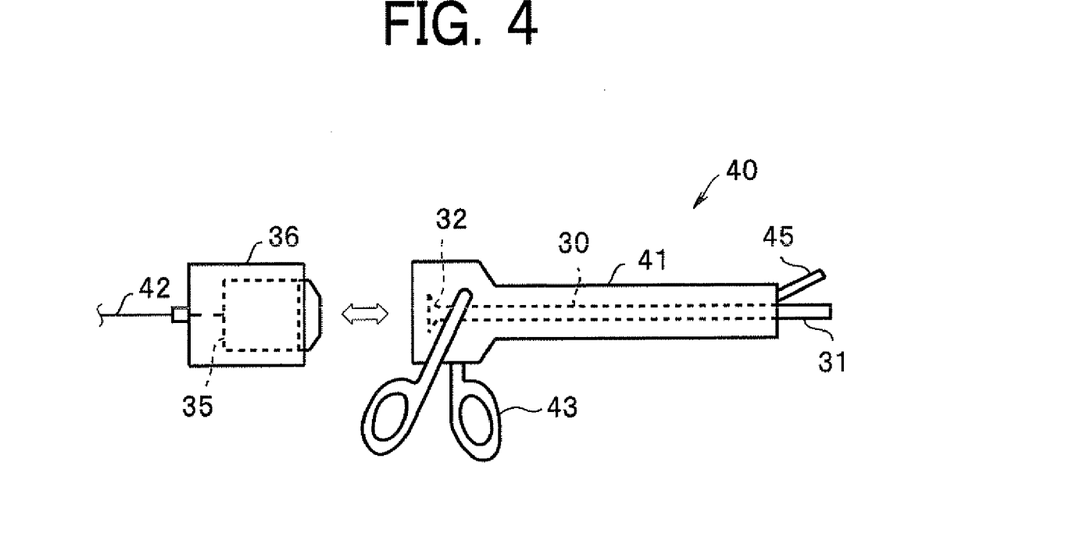
FIG. 4 is a schematic diagram illustrating the configuration of the probe of the ultrasound surgical apparatus according to the first embodiment.

Next, configuration of the handpiece 40 will be described further with reference to FIGS. 3 and 4. The transducer 35 is formed by stacking piezoelectric elements and electrodes. When a drive signal is applied to the electrodes of the transducer 35, the transducer 35 generates ultrasound vibrations.

A proximal end portion 32 of the probe 30 is screwed or otherwise mechanically coupled to the transducer 35 in a detachable manner. That is, before treatment, the surgeon attaches the probe unit 41 equipped with the probe 30 to be used for the treatment to the transducer 35 of the ultrasound unit 36. The probe 30 whose proximal end portion 32 is mechanically coupled with the transducer 35 transmits the ultrasound vibrations generated by the transducer 35 from the proximal end portion 32 to the distal end portion 31. The distal end portion 31 is a treatment portion used for treatment of living tissues by means of ultrasound vibrations. The treatment portion may be designed to be attachable and detachable to/from the probe 30.

Figure 5:
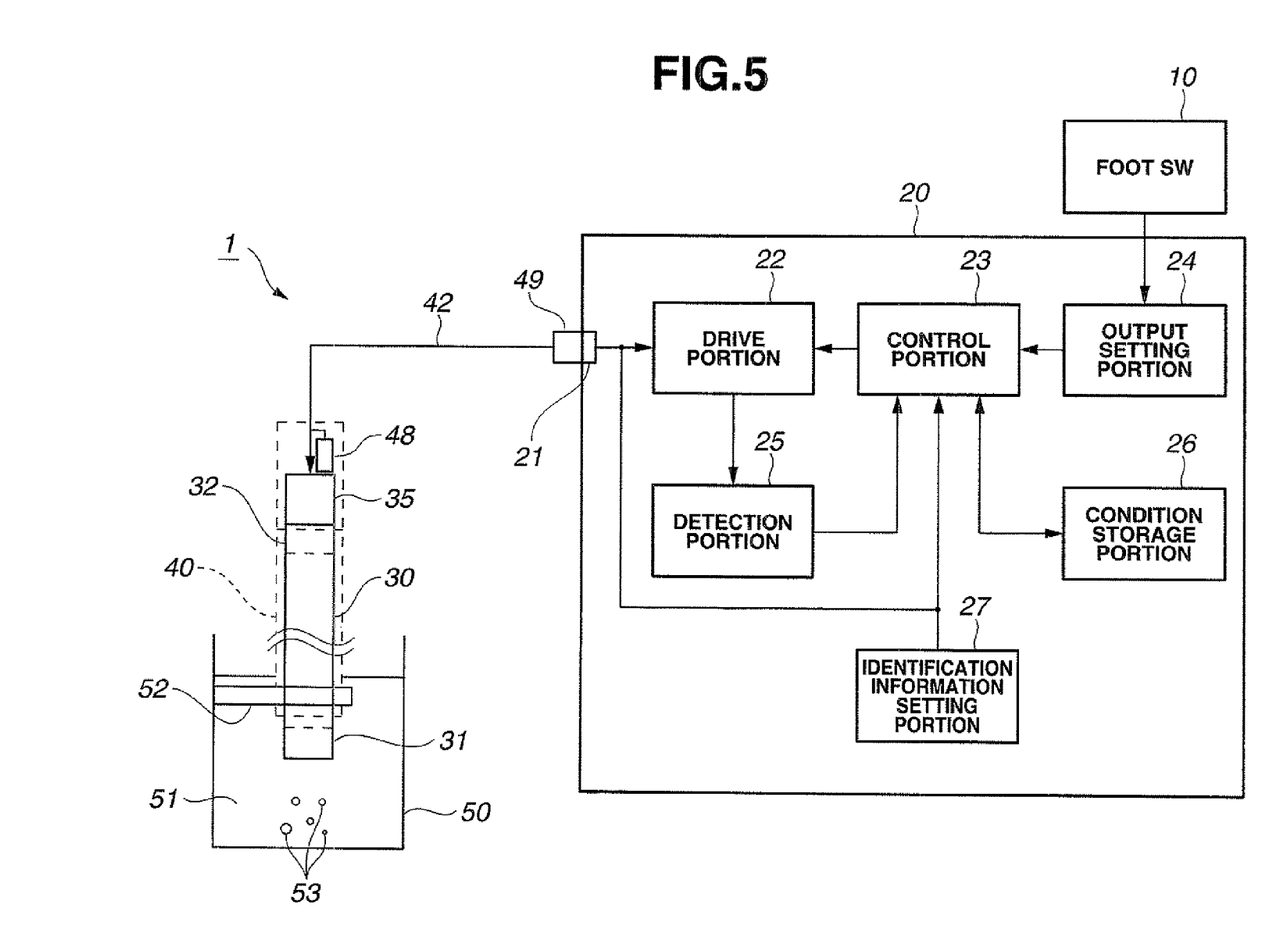
FIG. 5 is a block diagram illustrating a configuration of the ultrasound surgical apparatus according to the first embodiment.

Next, a configuration of, and a calibration method for, the ultrasound surgical apparatus 1 according to the present embodiment will be described with reference to FIG. 5. In FIG. 5, only the handpiece 40 and other components to be described are schematically shown.

As shown in FIG. 5, the apparatus body portion 20 of the ultrasound surgical apparatus 1 includes a drive portion 22, a control portion 23, an output setting portion 24, a detection portion 25, a condition storage portion 26, and a class information setting portion 27. Under the control of the control portion 23, the drive portion 22 outputs a drive signal to drive the transducer 35. The control portion 23 is, for example, a CPU which controls the entire ultrasound surgical apparatus 1 including the drive portion 22. That is, calibration, a calculation process, and the like described below are also controlled by the control portion 23. Of course, the ultrasound surgical apparatus 1 may include a calibration control portion which controls calibration separately from the control portion 23.

The output setting portion 24 sets output of the handpiece 40, i.e., vibration strength or amplitude of ultrasound vibrations in the distal end portion 31 based on an input signal from the foot switch 10 connected via the cable 13. The detection portion 25 detects a cavitation level signal (described later) during calibration of the ultrasound surgical apparatus 1. The condition storage portion 26 stores calibration information determined as a result of the calibration.

The class information setting portion 27 can set class information which can identify a class of the handpiece 40 connected to the apparatus body portion 20, where the class information may be, for example, an ID number, type information, or shape information of at least the transducer 35 or probe 30. For example, the ID number is a manufacturing number, model number, or the like; the type information is information about the type of handpiece 40 and the like; and the shape information is information about shape of the distal end portion 31 and the like of the probe 30.

On the other hand, the handpiece 40 has a class information storage portion 48 such as a ROM which stores the class information of the handpiece 40. The class information storage portion 48 stores class information which can also be set by the class information setting portion 27. The ultrasound surgical apparatus 1 can be connected with various types of handpieces 40. Each handpiece 40 is a combination of the transducer 35 and probe 30. Therefore, as described later, a first class information storage portion may be disposed in the ultrasound unit 36 and a second class information storage portion may be disposed in the probe unit 41 or probe 30. If the ultrasound surgical apparatus 1 is configured such that only the probe unit 41 or probe 30 is replaceable without the ultrasound unit 36 being replaced, only the probe unit 41 or probe 30 needs to have the class information storage portion 48.

If the identification information stored in the class information storage portion 48 or the identification information set by the class information setting portion 27 is an ID number such as a manufacturing number, the ultrasound surgical apparatus 1 may identify the class and the like of a corresponding handpiece with reference to the manufacturing number or the like stored in a memory (not shown) in the apparatus body portion 20 of the ultrasound surgical apparatus 1. The class information storage portion 48 may, for example, use resistance value for identification. The class information setting portion 27 may be configured to read a barcode put on the handpiece 40 or configured to be an ON-OFF arrangement of multiple switching elements such as dip switches.

As described above, the class information storage portion 48 and class information setting portion 27 have the same functions. Therefore, the ultrasound surgical apparatus 1 only needs to have at least one of the class information storage portion 48 and class information setting portion 27. Alternatively, the ultrasound surgical apparatus 1 may be configured to obtain identification information from the class information setting portion 27 when the identification information is not available from the class information storage portion 48, or conversely, to obtain identification information from the class information storage portion 48 when the identification information is not available from the class information setting portion 27.

The ultrasound surgical apparatus 1 according to the present embodiment has the configuration described above, and before treatment of a living tissue, the surgeon performs calibration using cavitation generated by the ultrasound emitted from the distal end portion 31.

As already described, for treatment, the ultrasound surgical apparatus 1 uses the frictional heat generated by the ultrasound vibrations of the distal end portion 31. Thus, for treatment, if there is not much water in the surroundings, ultrasound is not emitted from the distal end portion 31 to the surroundings. Even if ultrasound is emitted, the ultrasound does not have direct relevance to the treatment.

On the other hand, during calibration, the handpiece 40 is fixed by a fixing portion 52 of a calibration container 50 and the distal end portion 31 is kept immersed in a calibration solution 51. For calibration, the ultrasound surgical apparatus 1 generates cavitation, i.e., cavitation bubbles 53, in the calibration solution 51.

In order for cavitation of a certain level or higher to be generated by the ultrasound emitted from the distal end portion 31, vibration strength, i.e., vibration amplitude, has to be equal to or higher than a certain level. Drive signal strength needed to generate predetermined cavitation also varies with the type, shape, or the like of the handpiece. Therefore, the ultrasound surgical apparatus 1 prestores values of calibration signal strength for different classes of the handpiece 40 in the condition storage portion 26 or the like. Incidentally, the calibration signal strength is set to be suitable for calibration regardless of coagulation procedure signal strength and dissection procedure signal strength.

Calibration may be performed each time before treatment, only after the handpiece 40 or probe 30 is replaced, at predetermined time intervals, or before each use.

Figure 6:
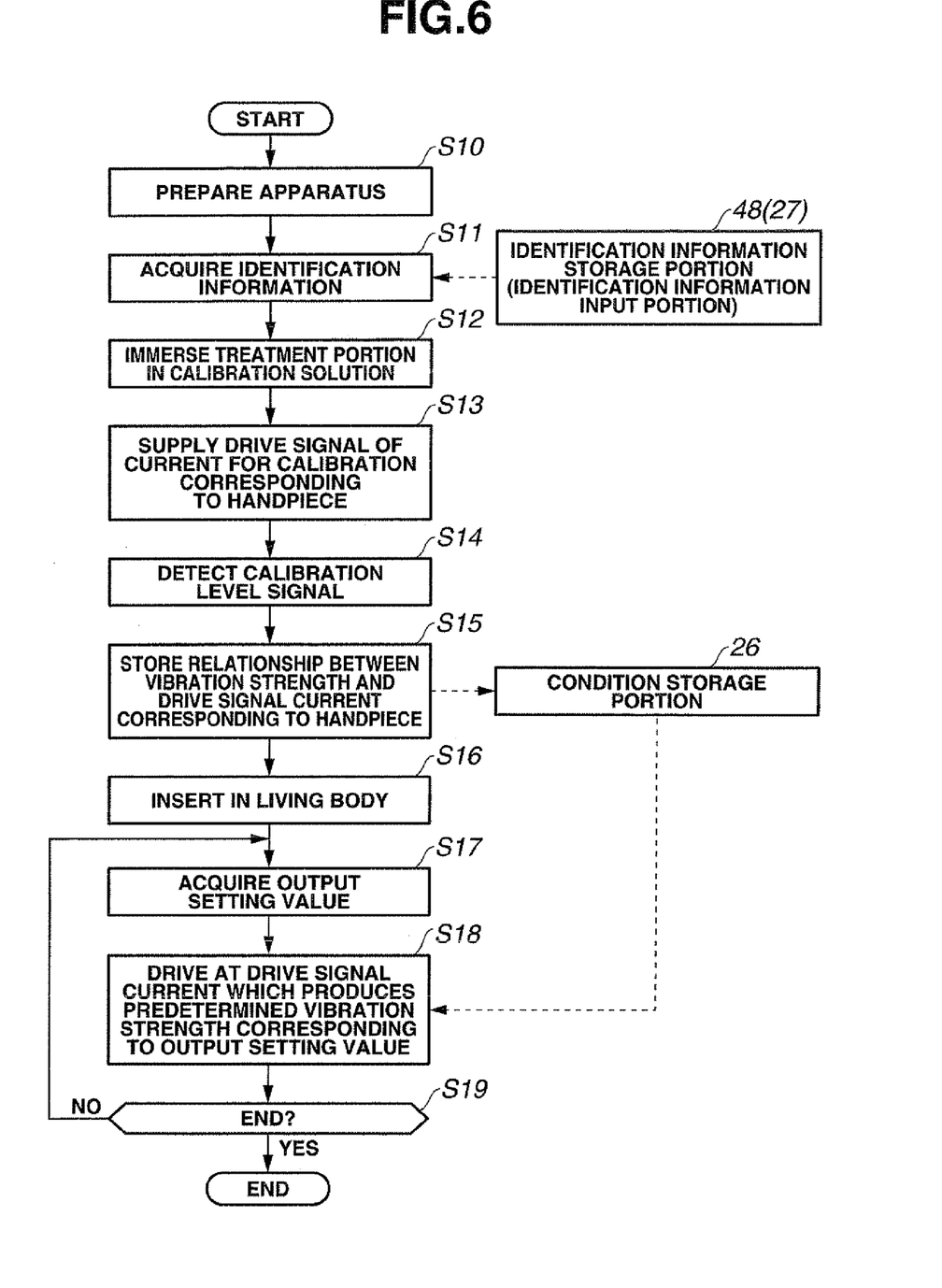
FIG. 6 is a flowchart illustrating a calibration method for the ultrasound surgical apparatus according to the first embodiment.

Next, a calibration method for the ultrasound surgical apparatus 1 will be described with reference to a flowchart in FIG. 6.

<Step S10> Preparation Step

The probe 30 is coupled to the transducer 35 and the handpiece 40 used for treatment is prepared. The connector 49 of the cable 42 of the handpiece 40 is connected to the socket 21 in the apparatus body portion 20 and the drive portion 22 is connected to the transducer 35.

<Step S11> Class Information Acquisition Step

Class information stored in the class information storage portion 48 of the handpiece 40 is acquired into the apparatus body portion 20. If class information is not available from the class information storage portion 48, the class information is acquired from the class information setting portion 27.

<Step S12> Distal End Portion Immersion Step

The calibration solution 51 is contained in the calibration container 50. The calibration solution 51 may be water, but a physiological saline solution is preferable. This is because a physiological saline solution is an inexpensive solution in which the type, solubility, and the like of a solute is controlled and which is readily available at a treatment location although conditions of cavitation occurrence varies depending on the type, solubility, and the like of the solute.

The calibration container 50 has the fixing portion 52 to fix the distal end portion 31 at a predetermined position. This is because too short a distance from the distal end portion 31 to a bottom or wall surface of the calibration container 50 will change conditions of cavitation occurrence.

<Step S13> Calibration Drive Signal Supply Step

When the ultrasound surgical apparatus 1 is ready for calibration, the surgeon instructs the ultrasound surgical apparatus 1 to start calibration, using a switch (not shown) or the like on the apparatus body portion 20. Consequently, the drive portion 22 supplies the transducer 35 with a drive signal of the calibration signal strength corresponding to the class information about the handpiece 40.

<Step S14> Cavitation Level Signal Detection Step

Ultrasound vibrations of the transducer 35 driven by the drive signal of the calibration signal strength are transmitted to the distal end portion 31 via the proximal end portion 32. Cavitation is generated in the calibration solution 51 by ultrasound emitted by the distal end portion 31. The detection portion 25 detects, in the drive signal, a cavitation level signal which corresponds to state of the cavitation. With the ultrasound surgical apparatus 1, the drive signal outputted by the drive portion 22 is a current-controlled signal with a frequency equal to resonance frequency $f_{res}$ of the transducer 35 which, for example, is 47 kHz.

Figure 7:
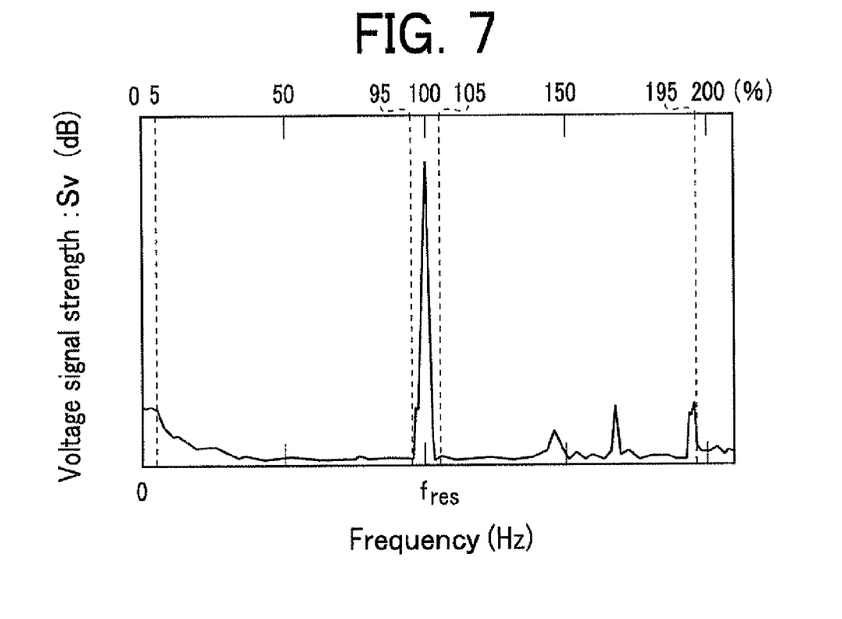
FIG. 7 is an explanatory diagram illustrating a cavitation level signal detected by a detection portion of the ultrasound surgical apparatus according to the first embodiment when no cavitation is generated.
Figure 8:
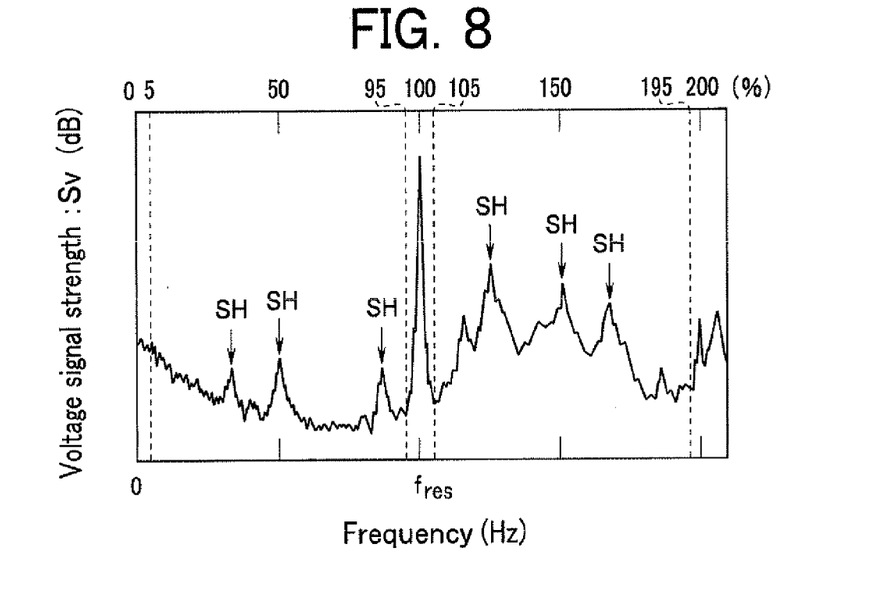
FIG. 8 is an explanatory diagram illustrating a cavitation level signal detected by the detection portion of the ultrasound surgical apparatus according to the first embodiment when cavitation is generated.

FIG. 7 shows a frequency spectrum distribution of a voltage signal Sv of the drive signal when no cavitation is generated. FIG. 8 shows a frequency spectrum distribution of the voltage signal Sv when cavitation is generated. The top side in both FIGS. 7 and 8 represents frequency when the resonance frequency $f_{res}$ is taken as 100%.

When no cavitation is generated as shown in FIG. 7, the voltage signal Sv does not have a large peak at frequencies other than the resonance frequency $f_{res}$. In contrast, when cavitation is generated as shown in FIG. 8, at frequencies other than the resonance frequency $f_{res}$, the voltage signal Sv has a higher level than when no cavitation is generated. That is, compared to when no cavitation is generated, when cavitation is generated, the voltage signal Sv has frequency peaks at ½, ¼, or other submultiples of the resonance frequency $f_{res}$ as well as at subharmonic (SH) frequencies, i.e., differences between the submultiples. Besides, at frequencies other than the subharmonic frequencies, the voltage signal Sv also has a higher level than when no cavitation is generated. As state of cavitation intensifies, the level of the voltage signal Sv shows more conspicuous differences from when no cavitation is generated, i.e., the level of the voltage signal Sv increases.

Consequently, by detecting the signal level of the voltage signal Sv of the drive signal at frequencies other than at or around the resonance frequency $f_{res}$ as a cavitation level signal, the detection portion 25 can detect the state of cavitation. For example, only frequency components 5% to 95% the resonance frequency $f_{res}$ can be acquired (integrated) by filtering the voltage signal and a resulting signal can be used suitably as the cavitation level signal. Alternatively, only frequency components between frequency 5% higher than the resonance frequency $f_{res}$ and frequency 5% lower than the second harmonic (2fres) frequency of the resonance frequency $f_{res}$ may be acquired by filtering the voltage signal and a resulting signal may be used as the cavitation level signal. Also, frequency components acquired by removing a 5% frequency component both above and below the resonance frequency $f_{res}$ may be used as the cavitation level signal. Furthermore, only subharmonic (SH) frequency components or peak strengths can be acquired and used suitably as the cavitation level signal.

Figure 9:
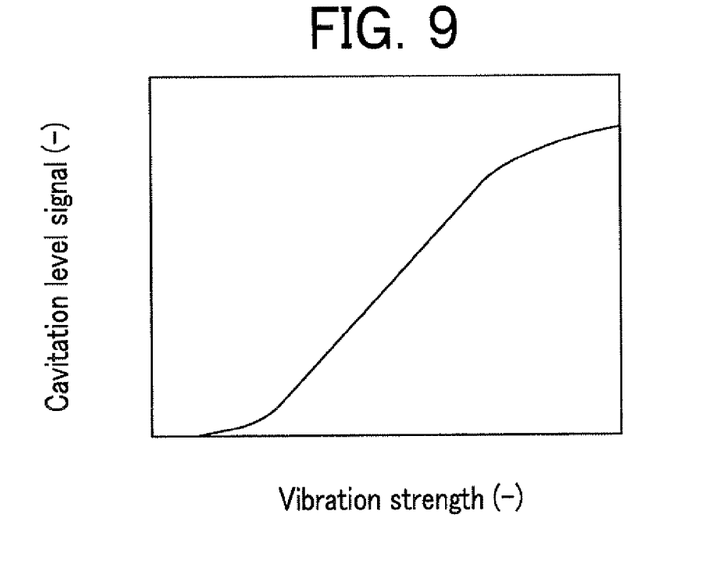
FIG. 9 is an explanatory diagram illustrating a relationship between the cavitation level signal detected by the detection portion of the ultrasound surgical apparatus according to the first embodiment and vibration strength of the distal end portion.

For example, FIG. 9 shows a relationship between a cavitation level signal acquired by integrating frequency components 5% to 95% the resonance frequency $f_{res}$ and the vibration strength, i.e., vibration amplitude, of the distal end portion 31. The cavitation level signal increases linearly with increases in the vibration strength. That is, the detection portion 25 can detect the state of cavitation using voltage values of the frequency components obtained by removing at least the frequency used for driving from the drive signal. The state of cavitation corresponds to the vibration strength of the distal end portion 31.

The cavitation level signal described above is not limited to a voltage signal, and may be an impedance signal. Also, if the drive portion 22 uses a voltage-controlled drive signal, the cavitation level signal may be a current signal.

<Step S15> Condition Storage Step

As already described, with the ultrasound surgical apparatus 1, even if the transducer 35 is driven at a predetermined driving current, the vibration strength of the distal end portion 31 varies due to manufacturing variations, operating temperature, state of junction between the transducer 35 and probe 30, aging of the apparatus, or the like.

Figure 10:
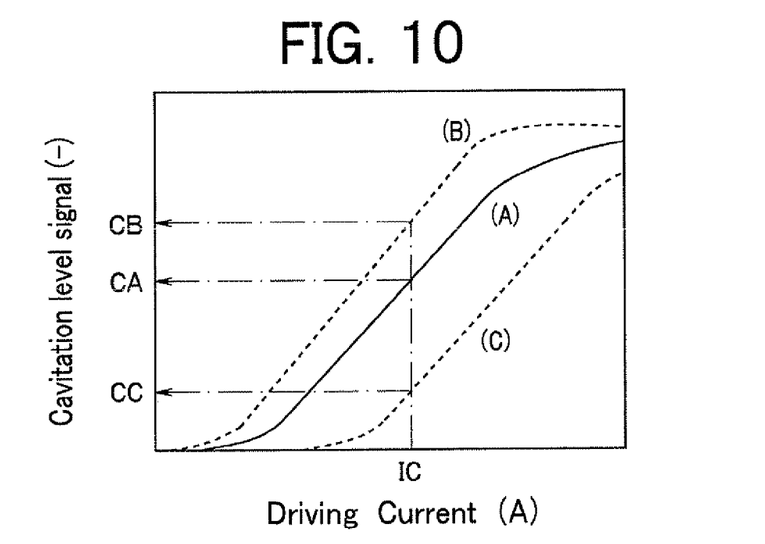
FIG. 10 is an explanatory diagram illustrating a relationship between drive signal strength and the cavitation level signal of the ultrasound surgical apparatus according to the first embodiment.

Specifically, as shown in FIG. 10, even when the transducer 35 is driven by a drive signal of a predetermined calibration signal strength IC, whereas CA is detected as a cavitation level signal in the case of handpiece A, CB stronger than CA may be detected in the case of handpiece B and CC weaker than CA may be detected in the case of handpiece C. As already described, the cavitation level signal corresponds to the vibration strength of the distal end portion 31.

Based on the calibration signal strength IC and cavitation level signal CA, CB, or CC, the ultrasound surgical apparatus 1 obtains calibration information represented by a relationship between the drive signal strength and actual vibration strength of the distal end portion 31. Then, the ultrasound surgical apparatus 1 stores the calibration information in the condition storage portion 26 by associating the calibration information with the class information.

The calibration information, for example, is a corrected drive signal strength obtained by correcting a standard drive signal strength used in a coagulation procedure or dissection procedure with a correction factor which is calculated as a ratio to a standard value of the cavitation level signal, where the ratio is expressed, for example, as CB/CA or CC/CA if the standard value of the cavitation level signal is CA. Alternatively, the correction factor may be stored as the calibration information. Furthermore, if the relationship between the drive signal strength and vibration strength is not linear, a drive signal strength correction formula may be used as the calibration information. That is, when the relationship between the drive signal strength and vibration strength is linear, the correction factor is a slope of the drive signal strength given by a linear expression.

<Step S16> Pre-Treatment Setup Step

Once the calibration is complete, the handpiece 40 is removed from the calibration container 50 and at least the distal end portion 31 of the handpiece 40 is inserted in a living body to treat living tissues.

<Step S17> Output Setting Step

By operating the foot switch 10 with a desired living tissue grasped between the grasping portion 45 and distal end portion 31, the surgeon sets the vibration strength of the distal end portion 31 to that for a coagulation procedure or dissection procedure via the output setting portion 24.

<Step S18> Treatment Step

When the foot switch 10 is operated, the drive portion 22 is controlled by the control portion 23 so as to output the corrected drive signal strength, i.e., the drive signal strength which, being based on the calibration information, corresponds to the vibration strength set by the output setting portion 24 for a coagulation procedure or dissection procedure.

If the calibration information is a correction formula, the control portion 23 controls the drive portion 22 by calculating corrected drive signal strength using the drive signal strength correction formula.

The vibrations of the transducer 35 driven by the drive signal of the corrected drive signal strength are transmitted to the distal end portion 31. Treatment of the desired living tissue is carried out using the ultrasound vibrations of the distal end portion 31.

<Step S19> End-Of-Treatment Determination Step

The ultrasound surgical apparatus 1 repeats steps from Step 17 until the treatment ends.

As described above, with the ultrasound surgical apparatus 1 according to the present embodiment, by performing calibration before treatment, it is possible to make the distal end portion 31 perform ultrasound vibrations always at predetermined vibration strength. Furthermore, since the ultrasound surgical apparatus 1 does not use a special apparatus, calibration can be performed easily at a treatment location.

Consequently, the ultrasound surgical apparatus 1 can make the distal end portion 31 perform ultrasound vibrations always at predetermined vibration strength regardless of not only manufacturing variations, but also operating temperature, state of junction between the transducer 35 and probe 30, aging of the ultrasound-activated scalpel, or the like. Thus, the ultrasound surgical apparatus 1 provides good operability.

Second Embodiment

Next, an ultrasound surgical apparatus 1A according to a second embodiment of the present invention will be described with reference to FIG. 11. The ultrasound surgical apparatus 1A according to the present embodiment is similar to the ultrasound surgical apparatus 1 according to the first embodiment, and thus components with the same functions as those of the first embodiment are denoted by the same reference numerals as the corresponding components in the first embodiment and description thereof will be omitted.

The ultrasound surgical apparatus 1A according to the second embodiment of the present invention can calibrate not only a scissors handpiece similar to the handpiece 40 according to the first embodiment, but also a different type or shape of handpiece 40X.

Figure 11:
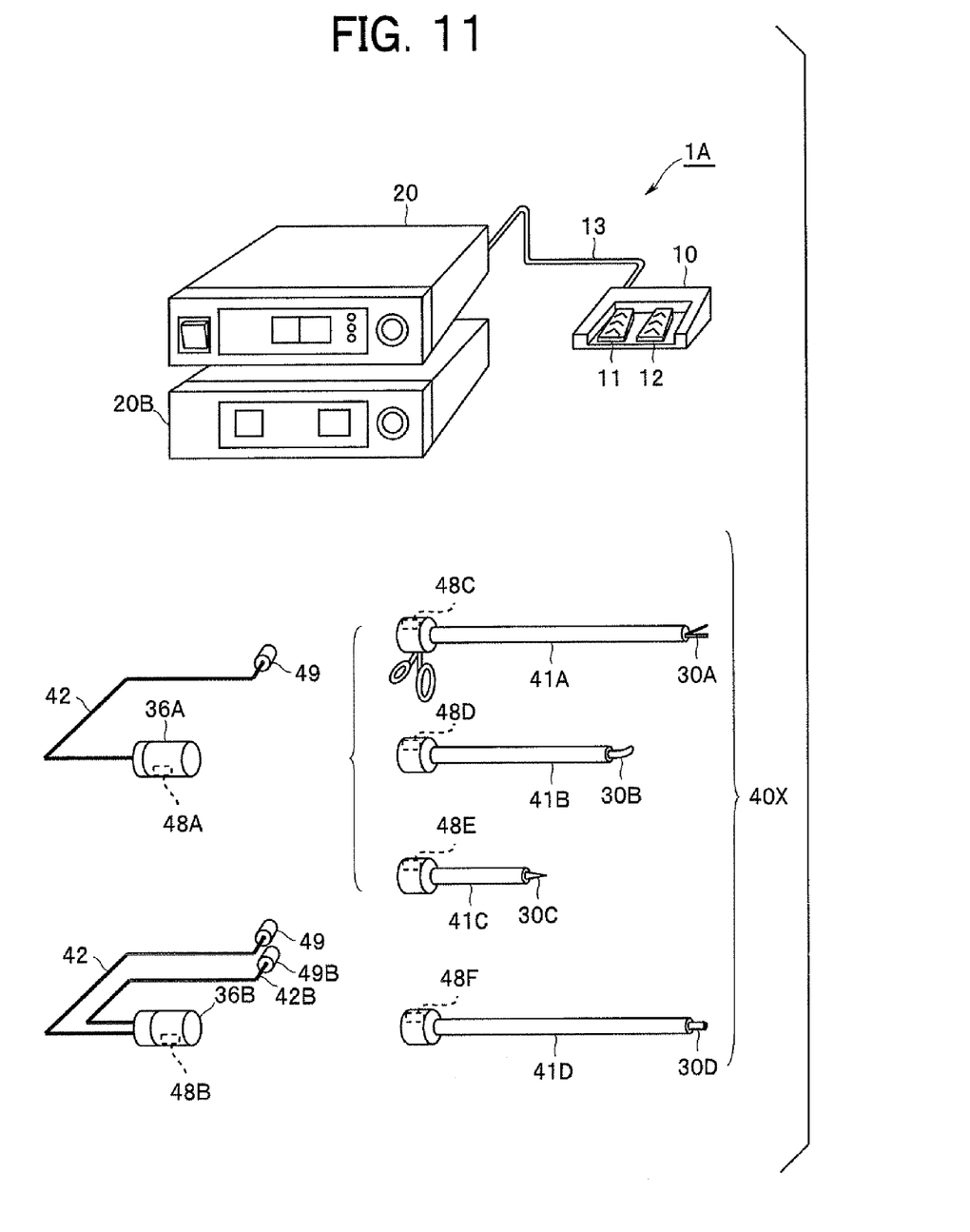
FIG. 11 is a block diagram illustrating a configuration of an ultrasound surgical apparatus according to a second embodiment.

That is, as shown in FIG. 11, a combination of an ultrasound unit 36A and a probe unit 41A equipped with a scissors probe 30A is a scissors handpiece similar to the handpiece 40 according to the first embodiment. Besides, a handpiece which is a combination of the ultrasound unit 36A and a probe unit 41B equipped with a hook (flex) probe 30B or a probe unit 41C equipped with a trocar probe 30C can also be used, being connected to the apparatus body portion 20. Furthermore, a handpiece which is a combination of the ultrasound unit 36B and a probe unit 41D equipped with an ultrasound aspiration probe 30D can also be used if a water supply and drainage tube 42B is connected to a water supply and drainage unit 20B via a connector 49B. Incidentally, although not illustrated, the water supply and drainage unit 20B is also connected with a foot switch.

Class information storage portions 48A and 4813 are disposed in the ultrasound units 36A and 36B, respectively while class information storage portions 48C to 48F are disposed in the probe units 41A to 41D, respectively. Consequently, in the ultrasound surgical apparatus 1A, the apparatus body portion 20 can identify an acoustic transducer of the connected handpiece as well as the ID number, type information, or shape information of the probe.

This allows the drive portion 22, control portion 23, and the like to perform processing according to various handpieces. The types of handpiece of the ultrasound surgical apparatus 1A are not limited to those described above. For example, the ultrasound surgical apparatus 1A may have a probe capable of applying a high-frequency current and use a handpiece capable of high-frequency current treatment.

The ultrasound surgical apparatus 11A according to the present embodiment not only provides the same advantages as those of the ultrasound surgical apparatus 1 according to the first embodiment, but also allows the type of handpiece to be selected according to the treatment, and thus has high versatility. Also, the calibration method for the ultrasound surgical apparatus 1A according to the present embodiment provides the same advantages as the calibration method for the ultrasound surgical apparatus 1 according to the first embodiment.

Thus, the ultrasound surgical apparatus and the calibration method for the ultrasound surgical apparatus according to the present invention are as follows.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasound surgical apparatus comprising:
   a handpiece equipped with an ultrasound transducer for generating ultrasound vibrations, and a probe provided with a proximal end portion coupled to the ultrasound transducer and a distal end portion to which the ultrasound vibrations are transmitted from the proximal end portion;
   a class information storage portion which is provided to the handpiece and stores identification information that indicates a class of the handpiece;
   a class information setting portion which, when connected to the handpiece, causes an electric signal to be transmitted from the class information storage portion to set the identification information;
   a drive portion which is connected to the ultrasound transducer and supplies the ultrasound transducer with a drive signal for generating the ultrasound vibrations;
   a detection portion which detects a signal level where only frequency components obtained by removing a resonance frequency of the drive signal are acquired, the signal level being a level of a cavitation level signal, the signal level corresponding to a state of cavitation generated when the distal end portion is vibrated with ultrasound in a calibration solution by a drive signal that causes vibration amplitude for calibration for causing the distal end portion of the probe to generate cavitation of a certain level corresponding to the identification information obtained via the class information setting portion;
   a correction relation calculation portion which, when the cavitation level signal as a predetermined drive signal is applied to the ultrasound transducer in one standard handpiece is regarded to have a standard value, calculates a correction relation of another handpiece with respect to the standard handpiece from a comparison relation of a cavitation level signal of the another handpiece with respect to the cavitation level signal having the standard value;
   a condition storage portion which, when a relation between a strength of the drive signal applied to the ultrasound transducer of the handpiece and an actual vibration strength at the distal end portion of the handpiece is regarded as calibration information, determines calibration information of the another handpiece with respect to calibration information of the standard handpiece based on the correction relation calculated by the correction relation calculation portion, and
   stores the calculated calibration information in advance before treatment is performed using the another handpiece; and
   a control portion which controls the drive signal to be supplied from the drive portion to the ultrasound transducer, based on the calibration information of the another handpiece stored in the condition storage portion, in order to cause the distal end portion to have a vibration strength suited for coagulation procedure or dissection procedure of a living tissue.

2. The ultrasound surgical apparatus according to claim 1, wherein the correction relation calculated by the correction relation calculation portion is a correction factor obtained from a ratio of a cavitation level signal of the another handpiece with respect to the cavitation level signal of the one standard handpiece having the standard value.

3. The ultrasound surgical apparatus according to claim 1, wherein the identification information is an ID number, type information, or shape information of at least the ultrasound transducer or the probe.

4. The ultrasound surgical apparatus according to claim 1, wherein the cavitation level signal is a voltage signal, a current signal, or an impedance signal.

5. The ultrasound surgical apparatus according to claim 1, wherein the cavitation level signal has the signal level obtained by integrating only frequency components acquired by removing a resonance frequency.

6. The ultrasound surgical apparatus according to claim 1, wherein the ultrasound transducer and the probe are coupled detachably.

7. The ultrasound surgical apparatus according to claim 1, further comprising a calibration container which contains the calibration solution and has a fixing portion used to fix the distal end portion at a predetermined position.

8. An ultrasound surgical apparatus comprising:
a handpiece equipped with an ultrasound transducer for generating ultrasound vibrations, and a probe provided with a proximal end portion coupled to the ultrasound transducer and a distal end portion to which the ultrasound vibrations are transmitted from the proximal end portion;
a class information storage portion which is provided to the handpiece and stores identification information that indicates a class of the handpiece;
a class information setting portion which, when connected to the handpiece, causes an electric signal to be transmitted from the class information storage portion to set the identification information;
a drive portion which is connected to the ultrasound transducer and supplies the ultrasound transducer with a drive signal for generating the ultrasound vibrations;
a detection portion which detects a signal level where only frequency components obtained by removing a resonance frequency of the drive signal are acquired, the signal level being, a level of a cavitation level signal, the signal level corresponding to a state of cavitation generated when the distal end portion is vibrated with ultrasound in a calibration solution by a drive signal that causes vibration amplitude for calibration for causing the distal end portion of the probe to generate cavitation of a certain level corresponding to the identification information obtained via the class information setting portion;
a correction relation calculation portion which, when the cavitation level signal as a predetermined drive signal is applied to the ultrasound transducer in one standard handpiece is regarded to have a standard value, calculates a correction relation of another handpiece with respect to the standard handpiece from a comparison relation of the cavitation level signal of the another handpiece with respect to the cavitation level signal having the standard value;
a condition storage portion which sets the correction relation calculated by the correction relation calculation portion as calibration information of the another handpiece and stores the calibration information in advance before treatment is performed using the another handpiece; and
a control portion which determines a relation between a strength of the drive signal to be applied to the ultrasound transducer in the another handpiece and an actual vibration strength of the distal end portion of the another handpiece with respect to a relation between a strength of the drive signal to be applied to the ultrasound transducer in the one standard handpiece and an actual vibration strength at the distal end portion of the standard handpiece, based on the calibration information of the another handpiece stored in the condition storage portion in order to cause the distal end portion to have a vibration strength suited for coagulation procedure or dissection procedure of a living tissue, and controls the drive signal to be supplied from the drive portion to the ultrasound transducer in accordance with the determined relation.

9. A calibration method for an ultrasound surgical apparatus comprising: a handpiece equipped with an ultrasound transducer for generating ultrasound vibrations, and a probe provided with a proximal end portion coupled to the ultrasound transducer and a distal end portion to which the ultrasound vibrations are transmitted from the proximal end portion; a class information storage portion which is provided to the handpiece and stores identification information that indicates a class of the handpiece; a class information setting portion which, when connected to the handpiece, causes an electric signal to be transmitted from the class information storage portion to set the identification information; and a drive portion which is connected to the ultrasound transducer and supplies a drive signal for generating the ultrasound vibrations to the ultrasound transducer, the method comprising:
a step in which the ultrasound transducer generates ultrasound vibrations;
a step in which the drive portion drives the ultrasound transducer by the drive signal;
a step in which the ultrasound transducer transmits ultrasound vibrations to a probe including a proximal end portion actively coupled to the ultrasound transducer and a distal end portion which generates ultrasound vibrations;
a step in which a class information storage portion acquires identification information of the handpiece;
a detecting step in which a detection portion detects a signal level where only frequency components obtained by removing a resonance frequency of the drive signal are acquired, the signal level being a level of a cavitation level signal, the signal level corresponding to a state of cavitation generated when the distal end portion is vibrated with ultrasound in a calibration solution by a drive signal that causes vibration amplitude for calibration for causing the distal end portion of the probe to generate cavitation of a certain level corresponding to the identification information obtained via the class information setting portion;
a correction relation calculation step in which a correction relation calculation portion, when the cavitation level signal as a predetermined drive signal is applied to the ultrasound transducer in one standard handpiece is regarded to have a standard value, calculates a correction relation of another handpiece with respect to the standard handpiece from a comparison relation of a cavitation level signal of the another handpiece with respect to the cavitation level signal having the standard value;
a condition storage step in which a condition storage portion, when a relation between a strength of the drive signal applied to the ultrasound transducer of the handpiece and an actual vibration strength at the distal end portion of the handpiece is regarded as calibration information, determines calibration information of the another handpiece with respect to calibration information of the standard handpiece based on the correction relation calculated by the correction relation calculation portion, and stores the calculated calibration information in advance before treatment is performed using the another handpiece; and
a control step in which a control portion controls the drive signal to be supplied from the drive portion to the ultrasound transducer, based on the calibration information of the another handpiece stored in the condition storage portion in order to cause the distal end portion to have a vibration strength suited for coagulation procedure or dissection procedure of a living tissue.

10. The calibration method for an ultrasound surgical apparatus according to claim 9, wherein the correction relation calculated by the correction relation calculation portion is a correction factor obtained from a ratio of a cavitation level signal of the another handpiece with respect to the cavitation level signal of the standard handpiece having the standard value.

11. The calibration method for an ultrasound surgical apparatus according to claim 9, wherein the identification information is an ID number, type information, or shape information of at least the ultrasound transducer or the probe.

12. The calibration method for an ultrasound surgical apparatus according to claim 9, wherein the ultrasound transducer and the probe are coupled detachably.

13. The calibration method for an ultrasound surgical apparatus according to claim 9, wherein the distal end portion is fixed to a predetermined position of a calibration container which contains the calibration solution.

14. A calibration method for an ultrasound surgical apparatus comprising: a handpiece equipped with an ultrasound transducer for generating ultrasound vibrations, and a probe provided with a proximal end portion coupled to the ultrasound transducer and a distal end portion to which the ultrasound vibrations are transmitted from the proximal end portion; a class information storage portion which is provided to the handpiece and stores identification information that indicates a class of the handpiece; a class information setting portion which, when connected to the handpiece, causes an electric signal to be transmitted from the class information storage portion to set the identification information; and a drive portion which is connected to the ultrasound transducer and supplies the ultrasound transducer with a drive signal for generating the ultrasound vibrations, the method comprising:

a detection step in which a detection portion detects a signal level where only frequency components obtained by removing a resonance frequency of the drive signal are acquired, the signal level being a level of a cavitation level signal, the signal level corresponding to a state of cavitation generated when the distal end portion is vibrated with ultrasound in a calibration solution by a drive signal that causes vibration amplitude for calibration for causing the distal end portion of the probe to generate cavitation of a certain level corresponding to the identification information obtained via the class information setting portion;

a correction relation calculation step in which a correction relation calculation portion, when the cavitation level signal as a predetermined drive signal is applied to the ultrasound transducer in one standard handpiece is regarded to have a standard value, calculates a correction relation of another handpiece with respect to the standard handpiece from a comparison relation of a cavitation level signal of the another handpiece with respect to the cavitation level signal having the standard value;

a condition storage step in which a condition storage portion sets the correction relation calculated by the correction relation calculation portion as cavitation information of the another handpiece and stores the calibration information in advance before treatment is performed using the another handpiece; and a control step in which a control portion determines a relation between a strength of the drive signal to be applied to an ultrasound transducer in the another handpiece and an actual vibration strength of the distal end portion of the another handpiece with respect to a relation between a strength of the drive signal to be applied to the ultrasound transducer in the one standard handpiece and an actual vibration strength at the distal end portion of the standard handpiece, based on the calibration information of the another handpiece stored in the condition storage portion in order to cause the distal end portion to have a vibration strength suited for coagulation procedure or dissection procedure of a living tissue, and controls the drive signal to be supplied from the drive portion to the ultrasound transducer in accordance with the determined relation.

* * * * *